United States Patent [19]

Rossomando

[11] 4,179,304

[45] Dec. 18, 1979

[54] FINGER NAIL LACQUER

[75] Inventor: Robert Rossomando, Branchburg, N.J.

[73] Assignee: Polychrome Corporation, Yonkers, N.Y.

[21] Appl. No.: 893,094

[22] Filed: Apr. 3, 1978

[51] Int. Cl.$^2$ .......................... C08L 1/18; A61K 7/043
[52] U.S. Cl. ..................................... 106/177; 106/162; 106/180; 106/181; 260/17.45 G; 260/17 R; 424/61
[58] Field of Search .................. 424/61; 106/162, 177, 106/180, 181; 260/17.45 G, 17 R

[56] References Cited

U.S. PATENT DOCUMENTS

| | | | |
|---|---|---|---|
| 3,076,718 | 2/1963 | Gearhart et al. | 106/180 |
| 3,216,840 | 11/1965 | Rouse et al. | 106/177 |
| 3,291,625 | 12/1966 | Faraone et al. | 106/177 |
| 3,478,756 | 11/1969 | Sautter et al. | 132/73 |
| 3,483,289 | 12/1969 | Michaelson et al. | 424/61 |
| 3,495,998 | 2/1970 | Reeves et al. | 106/176 |
| 3,503,909 | 3/1970 | Bowman et al. | 260/17 |

*Primary Examiner*—Earl A. Nielsen

[57] ABSTRACT

A composition is herein described which is capable of replacing carcinogenic formaldehyde containing resins in finger nail polish formulations. Said composition comprises:

a. A resin selected from the group consisting of sucrose benzoate and sucrose benzoate with polymeric methyl methacrylate;

b. Sucrose acetate isobutyrate;

c. An optional plasticizer selected from the group consisting of organic phthalates, organic adipates and organic phosphates.

10 Claims, No Drawings

FINGER NAIL LACQUER

BACKGROUND OF THE INVENTION

In the construction of prior art nail polish formulations it has been considered virtually indispensible to include a toluenesulfonamide/formaldehyde resin in the blend. Toluenesulfonamide/formaldehyde resin is important to provide the requisite adhesion of the nail polish blend to a subject finger nail. This resin has been shown to possess the necessary characteristics of gloss, hardness and resistance to household detergent solutions which are important to nail polishes. An important drawback to the use of this resin is the recent finding that formaldehyde is a carcinogen. However, until now, no satisfactory substitute for toluenesulfonamide/formaldehyde has been developed for nail polish formulations which possesses the necessary adhesion, gloss, hardness, detergent resistance and color stability properties.

SUMMARY OF THE INVENTION

As hereinbefore mentioned, the instant invention provides a substitute for toluenesulfonamide/formaldehyde resins in nail polish formulations whose degree of beneficial properties either equals or exceeds those of the prior art resin. The composition of the instant invention comprises:

a. A resin selected from the group consisting of sucrose benzoate and sucrose benzoate with polymeric methyl methacrylate, b. Sucrose acetate isobutyrate; and c. An optional plasticizer selected from the group consisting of organic phthalates, organic adipates, and organic phosphates.

This composition, when substituted for toluenesulfonamide/formaldehyde resin in nail polish formulations known to the skilled worker, either equals or exceeds the gloss, hardness, adhesion, detergent resistance and color stability characteristics of nail polishes employing toluenesulfonamide/formaldehyde resin.

It is therefore an object of the present invention to provide a nail polish lacquer which permits the elimination of toluenesulfonamide/formaldehyde resin from a nail polish formulation.

It is another object of the present invention to provide a nail polish lacquer which either equals or exceeds the gloss, adhesion, hardness, detergent resistance and color stability of nail polishes containing toluenesulfonamide/formaldehyde resin.

These and other objects of the instant invention will be in part discussed and in part apparent upon a consideration of the detailed description of the preferred embodiment.

DETAILED DESCRIPTION OF THE PREFERRED EMBODIMENT

Typical nail polish formulations include a film forming resin, an adhesion promoting composition, a solvent system, an optional colorant and a series of other optional ingredients which modify or control the various properties desired in a nail polish. Some of these properties include hardness, gloss, gloss retention, brittleness/softness balancing, detergent/water resistance, opacity, aroma, pH, color retention, evenness of flow, drying time, tackiness and cooperation of ingredients.

A typical nail polish formulation as sold by Revlon, Inc., of New York, has the following ingredients: butyl acetate, toluene, nitrocellulose, ethyl acetate, isopropyl alcohol, toluenesulfonamide/formaldehyde resin, dibutyl phthalate, camphor, stearalkonium hectorite, Quaternium-18 benzophenone-1, silica and malic acid. Such formulation may also contain mica, titanium dioxide, or other certified pigments.

As previously mentioned, the composition of the instant invention comprises:

a. A resin selected from the group consisting of sucrose benzoate and sucrose benzoate in admixture with polymeric methyl methacrylate; and b. Sucrose acetate isobutyrate; and c. An optional plasticizer selected from the group consisting of organic phthalates, adipates and phosphates.

Broadly, the sucrose benzoate may be present in the amount of from about 40 to 90%, polymeric methyl methacrylate may be present in an amount up to 20%, the sucrose acetate isobutyrate may be present in from about 5 to 30% and the plasticizer in an amount of from about 0 to 20%. All amounts are by weight based on total solids.

In one preferred embodiment, the sucrose benzoate is present in an amount of from about 60–90% and no polymeric methyl methacrylate is employed. In another more preferred embodiment the sucrose benzoate is present in an amount of from about 50 to 80% and polymeric methyl methacrylate is present in the amount of 10%.

Specific plasticizers useful within the context of the instant invention include:
Diethyl Adipate
Dibutyl Adipate
Diisobutyl Adipate
Dihexyl Adipate
Dicapryl Adipate
Di(2 Ethylhexyl) Adipate
Diisooctyl Adipate
Dinonyl Adipate
Octyl Decyl Adipate
Isooctyl Isodecyl Adipate
Didecyl Adipate
Diisodecyl Adipate
Isodecyl Octyl Adipate
Polypropylene Glycol Adipate
Dimethoxyethyl Adipate
Diethoxyethyl Adipate
Dibutoxyethyl Adipate
Dibutoxyethoxyethyl Adipate
Dimethyl Phthalate
Diethyl Phthalate
Dipropyl Phthalate
Dibutyl Phthalate
Diisobutyl Phthalate
Dihexyl Phthalate
Butyl Octyl Phthalate
Butyl Isodecyl Phthalate
Butyl Isohexyl Phthalate
Auryl Isohexyl Phthalate
Dioctyl Phthalate
Diisooctyl Phthalate
Dicapryl Phthalate
Di(2-Ethylhexyl) Phthalate
Dinomyl Phthalate
Diethyl Decyl Phthalate
Iso-octyl Isodecyl Phthalate
Didecyl Phthalate Ethylhexyldecyl Phthalate
Butyl Ethylhexyl Phthalate
Dimethoxyethyl Phthalate
2-Ethylhexyl diphenyl Phosphate
Modified Triaryl Phosphate Ester
Triphenyl Phosphate
Isodecyl Diphenyl Phosphate In forming a nail polish composition, the composition of the instant invention may be blended with any of a series of other ingredients to enhance or impart various properties. Such ingredients include film forming resins such as cellulose resins, particularly nitrocellulose. Other such resins may include cellulose propionate, cellulose acetate butyrate, ethyl cellulose and acrylic resins, especially Acryloid resins A-11, B-66, B-82, and NAD-10 available from Rohm & Haas.

In general, Acryloid resins are acrylic polymers, especially thermoplastic acrylic esters, more particularly, homopolymers and copolymers of alkyl acrylates and methacrylates.

When such other resins are employed it may be possible to reduce or even eliminate the plasticizer from the above formulation since these resins inherently possess some plasticizing properties. The selection of particular ingredients in any specific formulation of necessity must be selected by the skilled worker depending upon the specific properties sought to be obtained in the end product. Other such ingredients include solvents and colorants, particularly those officially certified by the U.S. Food and Drug Administration as useable in nail polish formulations. Still other ingredients conventionally employed in nail polish formulations may also be herein employed without departing from the spirit and scope of the instant invention.

These may include, but are not limited to, butyl acetate, toluene, ethyl acetate, isopropyl alcohol, dibutyl phthalate, camphor, stearialkonium hectorite, Quaternium-18 Benzophenone-1, silica and malic acid. Such formulation may also contain mica, titanium dioxide, or other certified pigments. Other ingredients which are well known in the art and conventionally included in nail polish formulations may also be included herein.

In a preferred embodiment, a commercially acceptable nail polish may include from about 5 to 20% of the hereinbefore described formulation comprising:

a. A resin selected from the group consisting of sucrose benzoate and sucrose benzoate in admixture with polymeric methyl methacrylate; and
b. Sucrose acetate isobutyrate; and
c. An optional plasticizer selected from the group consisting of organic phthalates, adipates and phosphates.

The remaining 80 to 95% may contain effective amounts of the above mentioned ingredients conventionally employed in nail polish formulations. The precise quantity of each is dependent upon the specific results sought to be achieved by the skilled worker.

EXAMPLES 1-3

The following compositions, according to the instant invention were formed:

|  | 1 | 2 | 3 |
|---|---|---|---|
| Sucrose Benzoate | 70% | 70% | 70% |
| Sucrose acetate isobutyrate | 22.2% | 22.2% | 22.2% |
| Butyl Benzyl Phthalate | 4.0% | — | — |
| Alkyl Phthalate | — | 4.0% | — |

-continued

|  | 1 | 2 | 3 |
|---|---|---|---|
| T-Butyl Phenyl Diphenyl Phosphate | — | — | 4.0% |
| Totuol | 3.8% | 3.8% | 3.8% |

EXAMPLES 4-7

A nail polish formulation was constructed as follows:

| | |
|---|---|
| 35% ¼" solvent soluble nitrocellulose, isopropanol wet, commercially available from Hercules, Inc., Wilmington, Del. 8.4% Ethyl Acetate 28.0% Butyl acetate 28.0% Toluol | 57.10% |
| Butyl benzyl phthalate | 6.70% |
| Isopropanol (99%) | 4.00% |
| Ethyl acetate | 1.70% |
| Butyl Acetate | 9.60% |
| Toluol | 13.50% |
| X | 7.40% |
| | 100.00% | wherein X is
(A) the composition of example 1
(B) the composition of example 2
(C) the composition of example 3
(D) toluenesulfonamide/formaldehyde resin available as resin MS-80 from Monsanto.

Formulations A, B, C, and D were then tested as follows:

A coating of each formulation was applied to a glass substrate using a commercially well known thin film applicator. After a 24 hour dry time, the following test results were noticed.

Gloss

Upon a visual inspection, each sample possessed equal gloss. Also, there was no noticeable loss in gloss after a one week time period had elapsed.

Adhesion

Each sample demonstrated approximately equally acceptable adhesion and hardness when tested with a Hoffman Scratch-Hardness tester. This is a device developed by E. E. Hoffman of the National Paint, Varnish and Lacquer Association in conjunction with E. I. Du Pont de Nemours and Co., Inc.

Water Resistance

The samples are immersed in water for 15 minutes and rubbed with a cloth. This procedure is repeated as necessary. Sample D failed after one such treatment. Samples A, B, and C failed after four such treatments indicating a superior water resistance to sample D.

Detergent Resistance

The water resistance experiment was repeated using a 3% Ajax ® solution. After one 15 minute treatment sample D failed whereas samples A, B, and C did not.

A pigment was then added to each formulation and the tests were repeated. Similar results were obtained.

Color Retention Test

A small bottle of formulations A, B, C, and D, are subjected to accelerated life testing by placing a small bottle of each sample in an oven at 140 degrees F. and tested for color retention periodically. After 24 hours, samples A, B, and C, demonstrated no substantial variation of shade as compared to an unbaked sample, whereas sample D demonstrated an unacceptable change in color from a water white to a distinctive yellow.

It is of course, to be understood that various modifications in the ingredients and proportions hereinbefore mentioned can be made without departing from the spirit and scope of the invention as defined by the claims appended hereafter.

What is claimed is:

1. A composition comprising,
   a. sucrose benzoate; and
   b. sucrose acetate isobutyrate; and
   c. an optional plasticizer selected from the group consisting of organic phthalates, adipates and phosphates; and
   d. nitrocellulose.

2. The composition of claim 1 further comprising an additional film forming resin.

3. The composition of claim 2 wherein said additional film forming resin is a cellulose resin.

4. The composition of claim 1 further comprising a composition selected from the group consisting of cellulose propionate, cellulose acetate butyrate, ethyl cellulose and acrylic resins.

5. The composition according to claims 1, 2, 3, or 5, further comprising a colorant.

6. The composition of claim 6, further comprising an organic solvent.

7. A composition comprising:
   from 17% to 21% ¼" solvent soluble nitrocellulose isopropanol wet
   from 5% to 7% ethyl acetate
   from 20% to 27% butyl acetate
   from 25% to 33% toluol
   from 5% to 7% butyl benzyl phthalate
   from 3% to 5% isopropanol
   from 0% to 10% colorant
   from 2% to 18% sucrose benzoate
   from 0% to 4% of a resin selected from the group consisting of cellulose propionate, cellulose acetate butyrate, ethyl cellulose and acrylic resins
   from 0.25% to 6% sucrose acetate isobutyrate
   from 0% to 4% of a plasticizer selected from the group consisting of organic phthalates, adipates and phosphates.

8. The composition of claim 4 wherein said acrylic resin is a homopolymer or copolymer of alkyl acrylates or methacrylates.

9. The composition of claim 1 further comprising from 0% to 4% of an acrylic resin, and wherein the sucrose benzoate is present in an amount from 2% to 18%, the sucrose acetate isobutyrate is present in an amount of from 1% to 6% and the plasticizer is present in an amount of from 0% to 4%, all in parts by weight.

10. A composition comprising:
    A. from 5 to 20% of a composition comprising,
       i. from 40 to 90% sucrose benzoate
       ii. from 0 to 20% acrylic resin
       iii. from 5 to 30% sucrose acetate isobutyrate
       iv. from 0 to 20% plasticizer selected from the group consisting of organic phthalates, adipates and phosphates
    B. from 17% to 21% nitrocellulose
    C. wherein the balance may comprise one or more compounds selected from the group consisting of colorants, organic solvents, film forming resins, organic phthalates, adipates and phosphates, camphor, silica, mica, stearalkonium hectorite and malic acid.

* * * * *